United States Patent [19]

Shuman et al.

[11] 4,216,317

[45] Aug. 5, 1980

[54] PROCESS FOR PREPARING ADENINE

[75] Inventors: Richard F. Shuman, Westfield; Roger J. Tull, Metuchen, both of N.J.

[73] Assignee: Merck & Co., Inc., Rahway, N.J.

[21] Appl. No.: 11,269

[22] Filed: Feb. 12, 1979

Related U.S. Application Data

[63] Continuation of Ser. No. 903,449, May 8, 1978, abandoned.

[51] Int. Cl.$^2$ .......................................... C07D 473/34
[52] U.S. Cl. .................................................... 544/277
[58] Field of Search ........................................ 544/277

[56] References Cited

U.S. PATENT DOCUMENTS

| | | | |
|---|---|---|---|
| 3,671,649 | 6/1972 | Yamara et al. | 544/277 |
| 4,059,582 | 11/1977 | Yonemitsu et al. | 544/277 |
| 4,100,159 | 7/1978 | Vanderzwan | 544/277 |

Primary Examiner—Nicholas S. Rizzo
Attorney, Agent, or Firm—Walter Patton; William H. Nicholson; Harry E. Westlake, Jr.

[57] ABSTRACT

Adenine is prepared by heating hydrogen chloride and hydrogen cyanide in a mixture of phosphorus oxychloride and dichlorophosphoric acid as solvent in a sealed vessel or by heating N-dichloromethylformamidine hydrochloride or triazine hydrochloride in a mixture of phosphorus oxychloride and dichlorophorphoric acid.

5 Claims, No Drawings

PROCESS FOR PREPARING ADENINE

This is a continuation of application Ser. No. 903,449, filed May 8, 1978.

SUMMARY OF THE INVENTION

This invention relates to a novel and improved method for producing adenine.

Adenine is a useful intermediate for the preparation of 6-amino-9-(substituted benzyl)purines, for example, those described in U.S. Pat. No. 3,846,426. Novel 6-amino-9-(substituted benzyl)purines are prepared by allowing an appropriately substituted benzyl halide, e.g., a substituted benzyl chloride, to react with adenine under the appropriate conditions. Oxidation of the resulting purine derivatives yields the corresponding $N^1$-oxides. These compounds, i.e., both the purine derivatives and the $N^1$-oxides thereof, have anticoccidial activity and are useful for controlling cecal and/or intestinal coccidiosis when administered in minor quantities to animals, in particular to poultry, usually in admixture with animal sustenance.

Heretofore, adenine has been synthesized from pyrimidine derivatives obtained by the reaction between malononitrile and thiourea, or by the reaction between malonic diamide and formamide, or by the reaction between formamidine and phenylazomalononitrile, or from 6-aminopurines having a halogen atom or mercapto group on the purine nucleus, or from imidazole derivatives (e.g. 4-aminoimidazole-5-carboxamide). It has also been synthesized by various modifications of the above-mentioned methods.

It has been reported that adenine was obtainable, though in very low yield, from hydrogen cyanide in the presence of ammonia. Recently, it has further been reported that adenine could be obtained in improved yields from hydrogen cyanide in the presence of ammonia under pressure.

More recently, it has further been reported that adenine can be prepared by subjecting formamide to the action of one of the oxyacids of phosphorus or of sulfur or the halides thereof which comprise phosphorus trichloride, phosphorus pentachloride, phosphorus oxychloride, phosphorus pentoxide, polyphosphoric acid, pyrophosphoric acid, thionyl chloride, sulfuryl chloride, chlorosulfonic acid and tosyl chloride.

However, these methods are less practical for the industrial production of adenine owing to the slightly more expensive starting materials and to the many and complicated steps as compared to the present process.

A principal object of this invention is to obviate the defects inherent in the prior art methods and to provide a novel process for producing adenine from HCN under acidic conditions and with a simple isolation procedure.

The aforesaid object is realized by heating hydrogen cyanide and hydrogen chloride in a mixture of phosphorus oxychloride and dichlorophosphoric acid as solvent. The novel process may be described by the following equation:

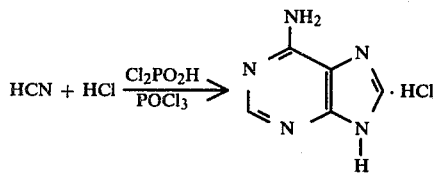

While the present process may be carried out in general when both starting materials are used in the molar ratio of 1:1, one of the starting materials may be employed in an excess amount if desired. The following molar ratios are used in carrying out this reaction:

| | |
|---|---|
| HCl:HCN | 1:2–10:1 |
| $POCl_3$:$Cl_2PO_2H$ | 1:2–4.5:1 (optimum ratio) |
| HCN:$Cl_2PO_2H$ | 1:2–2:1 |

The use of a mixture of phosphorus oxychloride ($POCl_3$) and dichlorophosphoric acid ($Cl_2PO_2H$) as a solvent is critical for obtaining the best yields of adenine. Phosphorus oxychloride alone or dichlorophosphoric acid alone under these conditions yields less then 15% adenine. The solvent can be prepared by mixing $POCl_3$ and $Cl_2PO_2H$ in the required proportion. A preferred method is to generate the required proportion of $POCl_3$ and $Cl_2PO_2H$ in situ by adding a calculated amount of water to $POCl_3$. This method of preparing the solvent has the advantage of producing HCl which is a required reagent in the reaction.

The reaction of the present invention is carried out under heating from about 100° C. to about 170° C. (preferably about 120° C. to about 150° C.) in a sealed vessel.

According to the present invention, the HCN and HCl in the above equation can be replaced by one-half mole of HCN dimer i.e. N-dichloromethylformamidine hydrochloride or one-third mole of HCN trimer i.e. triazine sesquihydrochloride or a yellow polymer of HCN as its HCl salt as described below in Examples 5 and 6, to obtain a comparable yield of adenine in the same solvent system and reaction conditions and temperature range.

The process can be illustrated by the following equations:

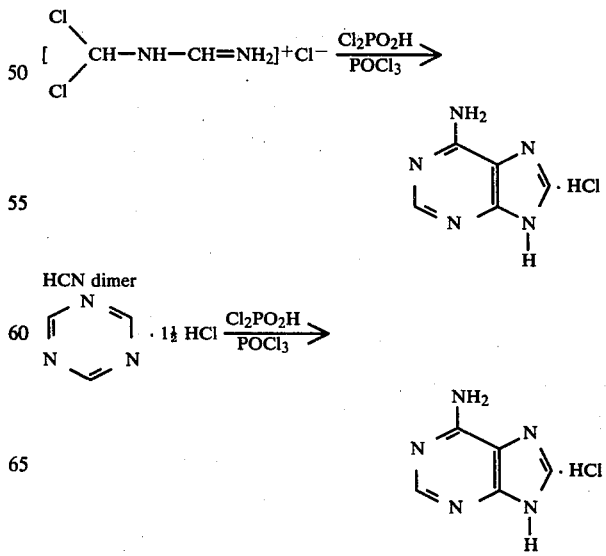

-continued

HCN trimer $(2HCN \cdot HCl)_x$ yellow polymer $\xrightarrow[POCl_3]{Cl_2PO_2H}$ wherein x is 200 to 500

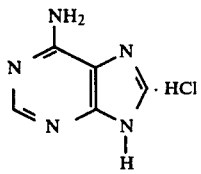 · HCl

Adenine thus obtained can be separated from the reaction mixture in a simple manner, e.g., by concentration of the reaction system, quenching, filtration and recrystallization. If necessary, purification processes using ion-exchange resins, adsorbents or the like may concomitantly be employed for isolating the adenine.

In the method of this invention, adenine is produced by a single step reaction and the isolation is very facile. Moreover, in the method of this invention, by-products which ordinarily render the separation and purification of adenine difficult, are largely soluble and easily removed by recrystallization.

The following examples set forth presently preferred illustrative, but not limitative embodiments of the invention.

EXAMPLE 1

Preparation of Mixtures Containing Phosphorus Oxychloride ($POCl_3$) and Dichlorophosphoric Acid ($Cl_2PO_2H$)

Mixtures of $POCl_3$ and $Cl_2PO_2H$ in a ratio of 1:1 are most conveniently prepared by carefully adding one mole of water to two moles of $POCl_3$. Other ratios of these reagents may be prepared by adjusting the amount of water according to the amount of $Cl_2PO_2H$ desired. This is in accordance with the principles set forth in J. R. Van Wazer and E. Flusk, *J. Am. Chem. Soc.*, 81, 6360 (1959) which is herein incorporated by reference. The reaction of $POCl_3$ with water is explained by the following equation:

$$POCl_3 + H_2O \rightarrow Cl_2PO_2H + HCl$$

EXAMPLE 2

Preparation of Adenine from HCN, HCl, $POCl_3$ and Water

To two moles of $POCl_3$ (307 g., 104 ml.) was added one mole of water over a 45 minute period. The internal temperature was maintained at about 20° to 25° C. by cooling with an ice-bath. The exothermic reaction temperature did not exceed 27° C. To the resulting solution of $POCl_3$, dichlorophosphoric acid and HCl (hydrogen chloride) was added one mole HCN (27 g., 39 ml.). The solution was cooled to 0° C. and saturated with 0.4 mole anhydrous HCl (14.5 g.).

The solution was placed in a glass lined rocking bomb with approximately two volumes of head space and heated at 120° C. for 15 hours. The maximum pressure was 87 psig and the final pressure after cooling to 25° C. was 32 psig.

At the end of the reaction period, the excess $POCl_3$ (50 ml., 0.545 moles) was recovered by vacuum distillation. The residue (272 g.) was quenched into 200 ml. of methanol at 60° C. over a 30 minute period. The solids were collected by filtration and washed with 50 ml. methanol and ether ($2 \times 50$ ml.) with slurring. The product was dried overnight in vacuo at 60° C. to yield a dark, damp solid weighing 45.9 g. The crude cake contained 7.6 g. of adenine.

The crude cake was suspended in 60 ml. hot water. The dark insoluble material was filtered and washed with 5 ml. hot water. The filtrate and washings were allowed to cool to 45° C. and seeded with crystals of adenine hydrochloride hemihydrate. The seeded solution was cooled to 25° C. over a 4 hour period and aged at 0° C. for 18 hours. The solid was collected by filtration, washed with 15 ml. cold isopropyl alcohol:water (3:1) and dried in vacuo to constant weight at 75° C. The solid weighed 7.4 g. and contained adenine.H-Cl½$H_2O$ of about 88% purity.

EXAMPLE 3

Preparation of Adenine from N-Dichloromethylformamidine Hydrochloride (HCN dimer)

To a solution of 100 ml. of phosphorus oxychloride ($POCl_3$) and 100 ml. of dichlorophosphoric acid ($Cl_2PO_2H$) was added 22.2 g. of N-dichloromethylformamidine hydrochloride [prepared by the process set forth in E. Allenstein, A. Schmidt, and V. Beylo, *Chemische Berichte*, 99, 431 (1966) by treating an ethereal solution of HCN with hydrogen chloride at −15° C.] This mixture was placed in an autoclave and heated at 130° C. for 15 hours. Assay of the cooled solution by high pressure liquid-liquid chromatography showed the yield of adenine to be 2.78 g. (38%). The isolation of the adenine is carried out as set forth in Example 2.

EXAMPLE 4

Preparation of Adenine from 1,3,5-Triazine Sesquihydrochloride, $POCl_3$ and Water To two moles of $POCl_3$ (307 g., 104 ml.) was added one pole of water over a 45 minute period. The internal temperature was maintained at about 20° to 25° C. by cooling with an ice-bath. The exothermic reaction temperature did not exceed 27° C. To the resulting solution was added 0.33 mole of triazine sesquihydrochloride (135.75 g.) [prepared by heating N-dichloromethylformamidine hydrochloride as described in C. Grundmann and A. Kreutzberger, *J. Am. Chem. Soc.*, 76, 5646 (1954)]. The solution was cooled to 0° C. and saturated with 0.4 mole anhydrous HCl (14.5 g.).

The solution was placed in a glass lined rocking bomb with approximately two volumes of head space and heated at 120° C. for 15 hours. The maximum pressure was 87 psig and the final pressure after cooling to 25° C. was 32 psig.

At the end of the reaction period, the excess $POCl_3$ (50 ml., 0.545 moles) was recovered by vacuum distillation. The residue (272 g.) was quenched into 200 ml. of methanol at 60° C. over a 30 minute period. The solids, containing adenine, were collected by filtration, washed with 50 ml. methanol and ether $2 \times 50$ ml. with slurring and dried overnight in vacuo at 60° C.

The crude cake was suspended in 60 ml. hot water. The dark insoluble material was filtered off and washed with 5 ml. hot water. The filtrate and washings were allowed to cool to 45° C. and seeded. The seeded solution was cooled to 25° C. over a 4 hour period and aged at 0° C. for 18 hours. The solid was collected by filtration, washed with 15 ml. cold isopropyl alcohol:water (3:1) and dried in vacuo to constant weight at 75° C. The solid contained adenine.HCl.½H$_2$O.

EXAMPLE 5

Preparation of Yellow Polymer of Hydrogen Cyanide

Phosphorus oxychloride (1.227 kg, 8 moles) was cooled to 5° C. and over 1 hour at 5° to 10° C. there was added formamide (181 g. 4 moles). The mixture was warmed to 30° C. and it slowly exothermed to 40° C. The reaction mixture was maintained at 40°–45° C. with cooling until heat evolution subsided after 45 minutes. During this time vapors of hydrogen cyanide were condensed and returned to the reaction. The mixture was placed in a glass-lined autoclave, sealed, and heated at 90°–95° C. for one hour. After cooling, the pale yellow solid was filtered, washed with 100 ml. of POCl$_3$ and then with 300 ml. of diethyl ether. The product was dried in vacuo to a constant weight of 38.4 g. When heated this product darkens and partially sublimes, and the residue decomposes with vigorous gassing at 210°–215° C. This polymer is composed of approximately two parts of HCN and one part of HCl and a trace of phosphorus. It has the ratio of elements as follows: $C_{12}H_{12}N_{12}.6HCl.H_3PO_4$ and is not soluble in dimethyl sulfoxide and is decomposed by water. The molecular weight of the polymer, exclusive of HCl and H$_3$PO$_4$, is in the range of about 324 to about 972.

The percentage of elements found in the polymer is as follows:
C, 20.98%
H, 4.26%
N, 29.08%
Cl, 37.06%
P, 4.0%

EXAMPLE 6

Preparation of Adenine from Yellow Polymer of HCN

Yellow polymer (9.1 g.) composed of two parts of hydrogen cyanide with one part of hydrogen chloride was placed in a 1:1 solution (50 ml.) of POCl$_3$ and Cl$_2$PO$_2$H and heated in a glass-lined autoclave at 130° C. for 15 hours. The cooled, yellow solution was quenched over 400 g. of ice and diluted to a final volume of 500 ml. with water. This solution was assayed by quantitative high pressure liquid-liquid chromatography which showed the presence of 1.7 g. of adenine.

What is claimed is:

1. A process for the preparation of adenine consisting of:
    heating in a sealed vessel the reactants, HCN, HCl, in Cl$_2$PO$_2$H and POCl$_3$ wherein the sealed vessel is heated to about 120° C. to 150° C. for about 15 hours with a maximum internal pressure of about 87 psig and a final temperature of about 25° C. and internal pressure of about 32 psig and the molar ratio HCl:HCN is 1:1; the molar ratio POCl$_3$:Cl$_2$PO$_2$H is 1:2–4.5:1; and the molar ratio HCN:Cl$_2$PO$_2$H is 1:1.

2. A process according to claim 1 wherein the Cl$_2$PO$_2$H is prepared from water and POCl$_3$ wherein the molar ratio HCl:HCN is 1:2–10:1; the molar ratio POCl$_3$:Cl$_2$PO$_2$H is 1:2 to 4.5:1; and the molar ratio HCN;Cl$_2$PO$_2$H is 1:2–2:1.

3. A process for the preparation of adenine consisting of:
    heating in a sealed vessel N-dichloromethylformamidine hydrochloride in Cl$_2$PO$_2$H and POCl$_3$ wherein the sealed vessel is heated to about 120° C. to 150° C. for about 15 hours with a maximum internal pressure of about 87 psig and a final temperature of about 25° C. and internal pressure of about 32 psig and the molar ratio POCl$_3$:Cl$_2$PO$_2$H is 1:2–4.5:1.

4. A process for the preparation of adenine consisting of:
    heating in a sealed vessel triazine hydrochloride in Cl$_2$PO$_2$H and POCl$_3$ wherein the sealed vessel is heated to about 120° C. to 150° C. for about 15 hours with a maximum internal pressure of about 87 psig and a final temperature of about 25° C. and internal pressure of about 32 psig and the molar ratio POCl$_3$:Cl$_2$PO$_2$H is 1:2–4.5:1.

5. A process for the preparation of adenine consisting of:
    heating in a sealed vessel yellow polymer of hydrogen cyanide as its hydrochloride salt in Cl$_2$PO$_2$H and POCl$_3$ wherein the sealed vessel is heated to about 120° C. to 150° C. for about 15 hours with a maximum internal pressure of about 87 psig and a final temperature of about 25° C. and internal pressure of 32 psig and the molar ratio POCl$_3$:Cl$_2$PO$_2$H is 1:2–4.5:1.

* * * * *